US008586089B2

(12) United States Patent
Anderson

(10) Patent No.: US 8,586,089 B2
(45) Date of Patent: Nov. 19, 2013

(54) ENHANCED CARRIERS FOR THE DELIVERY OF MICROPARTICLES TO BODILY TISSUES AND FLUIDS

(76) Inventor: Russell J. Anderson, San Diego, CA (US)

( * ) Notice: Subject to any disclaimer, the term of this patent is extended or adjusted under 35 U.S.C. 154(b) by 589 days.

(21) Appl. No.: 12/348,290

(22) Filed: Jan. 3, 2009

(65) Prior Publication Data

US 2010/0172829 A1 Jul. 8, 2010

(51) Int. Cl.
*A61K 51/12* (2006.01)
(52) U.S. Cl.
USPC ............................ 424/488; 424/484; 424/486

(58) Field of Classification Search
USPC ................................................. 424/485–490
See application file for complete search history.

(56) References Cited

U.S. PATENT DOCUMENTS 5,344,452 A * 9/1994 Lemperle .................. 623/23.73
2002/0176893 A1* 11/2002 Wironen et al. ............. 424/489
2003/0119985 A1* 6/2003 Sehl et al. .................... 525/54.1
2007/0190101 A1* 8/2007 Yang et al. .................... 424/423

FOREIGN PATENT DOCUMENTS

EP 0747067 12/1996

* cited by examiner

*Primary Examiner* — Michael G Hartley
*Assistant Examiner* — Micah-Paul Young
(74) *Attorney, Agent, or Firm* — Harris F. Brotman

(57) ABSTRACT

Improved compositions for tissue augmentation are provided. These compositions comprise an amount of crosslinked material sufficient to provide a melt temperature ($T_m$) greater than 37C, wherein microparticles can be substantially uniformly dispersed and maintained at ambient room temperature as well as body temperature. Said compositions also provide high shear moduli, sufficient to effectively deliver microparticles into dense tissue and narrow intersticial spaces without significant disruption to the homogeneous distribution of microparticles within the solution. The provided compositions can be stored and shipped at room temperature without significant detriment to the material composition. Additional embodiments include a system for delivery of tissue augmentation materials and methods of manufacture thereof.

15 Claims, 1 Drawing Sheet

ENHANCED CARRIERS FOR THE DELIVERY OF MICROPARTICLES TO BODILY TISSUES AND FLUIDS

FIELD OF THE INVENTION

The present invention relates to medical implants and, more particularly, to the delivery of microspheres, microparticles and other components for insertion into the patient's body to achieve augmentation or repair of tissues or anatomical structures.

BACKGROUND OF INVENTION

Microspheres and microparticles, such as described in U.S. Pat. Nos. 5,344,452, and 7,442,389, the entire contents of which are incorporated herein by reference, made of for example polymethylmethacrylate (PMMA) or other materials, are currently combined with foreign carrier materials (e.g., gelatinous bovine collagen) and injected or introduced into the body to accomplish augmentation or repair of various tissues or anatomical structures. The gelatinous bovine collagen has been used as the carrier of choice due to its' many favorable attributes, including its' ability to hold the microspheres in suspension below certain temperatures, its' tissue healing and cell generation properties, and its' low immune response rate in humans The use of largely denatured gelatinous bovine collagen as a carrier for such microspheres and microparticles has several major drawbacks. The melting point of the largely denatured gelatinous bovine collagen (the $T_m$ for gelatinous 3.5% collagen is approximately 26.5° C.) is well below the normal body temperatures, and as such those microspheres and microparticles settle out of suspension when exposed to temperatures well below normal body temperatures and even at higher end room temperatures. The resorption rate of the gelatinous bovine collagen in the human body is also only a matter of a few days, which does not allow sufficient time for host tissue to completely replace the carrier material before it is absorbed into the body, removing the anchoring support structure around the microparticles before they can be supported by new host tissue. Additionally, the gelatinous bovine collagen carrier must be stored and handled quickly at refrigeration temperatures in order to maintain the microspheres in uniform suspension. It is also undesirable because the extrusion forces necessary to express the gelatinous bovine material from a syringe at those temperatures are excessive. In addition, the gelatinous bovine collagen and other gel carriers do not have sufficient shear resistance and resistance to deformation to adequately push the microspheres or microparticles into dense tissue while maintaining the necessary homogenous distribution.

There exists a need for enhanced carrier materials capable of providing properties that solve the issues stated above, so that microspheres and microparticles can be effectively delivered into patient tissues and anatomical structures for augmentation or repair.

SUMMARY OF THE INVENTION

The present invention addresses these needs by providing enhanced carrier materials for use in the delivery of microspheres and microparticles into patients' tissues and anatomical structures for augmentation and repair procedures. Use of these enhanced carriers as the delivery vehicle for microparticles can improve the delivery effectiveness, the physiological effectiveness, and the delivery ease and accuracy. These enhanced carriers will also reduce the storage and handling requirements, and provide a viable means for the delivery of uniformly distributed microparticles into dense tissues and interstitial spaces that were previously unreachable, and allowing the treatment of a large number of new physiological indications that were previously untreatable.

In accordance with certain aspects of the present invention, objects and advantages of the methods and features described herein may include one or more of the following: a) providing a biocompatible augmentation or repair material that is able to maintain its' homogeneity and effectiveness at temperatures above that of body temperature; b) providing a biocompatible augmentation or repair material that is far more effective because it can deliver a homogeneous distribution of microspheres into dense tissue and small interstitial spaces due to its' higher resistance to deformation, dramatically improved shear modulus, and better dynamic viscosity; c) providing a biocompatible augmentation or repair material that does not require refrigeration in order to maintain the microspheres in suspension; d) providing a biocompatible augmentation and repair material that does not require excessive plunger extrusion forces in order to deliver through a small bore needle; e) providing a biocompatible augmentation or repair material that is more effective because the resorption rate of the carrier is long enough to allow the patients' own tissue to grow around the microparticles as the carrier material is being absorbed by the body; f) providing a biocompatible augmentation or repair material that can be safely injected into the patients' body, comprising microparticles blended with a carrier material further comprising a controlled ratio mixture of crosslinked native collagen and denatured gelatinous collagen or other biocompatible gelatin which can contain other desirable materials, such as but not limited to one or more of an anti inflammatory agent, an antibiotic agent, an anesthetic agent, an adhesive agent, an adhesion prevention agent, a hemostatic agent, a coagulant agent, a preservative agent, a gelation agent, a growth factor agent, and/or a radiopaque indicator or other contrasting agent.

Any feature or combination of features described herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described herein. Of course, it is to be understood that not necessarily all such aspects, advantages or features will be embodied in any particular embodiment of the present invention. Additional advantages and aspects of the present invention are apparent in the following detailed description and claims that follow.

DETAILED DESCRIPTION OF THE PREFERRED EMBODIMENTS

Figure 1:
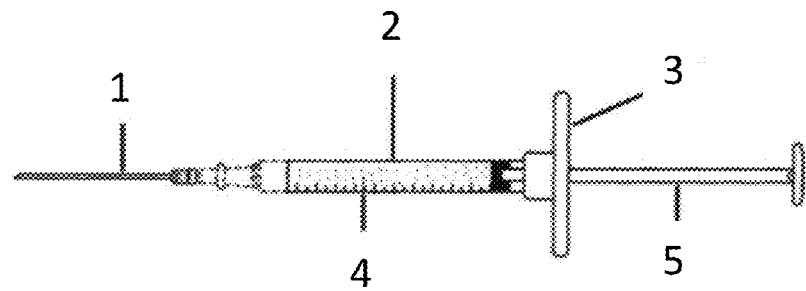
FIG. 1 is a detailed view of the syringe delivery system containing a material for injection in accordance with one embodiment of the present invention.

Although the disclosure herein refers to certain described embodiments, it is to be understood that embodiments presented herein are by way of example and not by way of limitation. The intent of this disclosure, while discussing exemplary embodiments, is that the following detailed description be construed to cover all modifications, alternatives, and equivalents of the embodiments as may fall within the spirit and scope of the invention as defined by the appended claims. It is to be understood and appreciated that the process steps and formulations described herein do not cover a complete process flow for operations involving compounding, tissue augmentation, and repair. The present invention may be practiced in conjunction with various techniques that are conventionally used in the art, and only so much of the commonly practiced process steps are included herein as are necessary to provide an understanding of the present invention.

The methods and systems described herein can allow physicians to repair, treat or augment a patient's tissue or fluids using an enhanced tissue treatment implant which may take the form of a biocompatible augmentation or repair material. The tissue treatment material can comprise microparticles and a biocompatible carrier medium in the form of a mixture of cross linked native bovine or other mammalian collagen blended with partially denatured gelatinous bovine or other mammalian collagen or biocompatible gelatin, with the ratios of those two components being controlled. In one aspect of the present invention, the denatured gelatinous bovine or other mammalian, avian or reptilian collagen provides the ability to hold the microparticles uniformly in suspension after blending. In another aspect of the present invention, the microparticles are substantially uniformly suspended within the biocompatible carrier at ambient temperature, thus making storage of the product less costly and more environmentally and functionally suitable.

In one embodiment, the crosslinked native fibrillar mammalian, avian or reptilian collagen component comprises a melting point greater than 37.0° C. In one preferred embodiment the $T_m$ will be in the range of about 37.0° C. to about 65.0° C.

In another embodiment, the crosslinked native fibrillar mammalian, avian or reptilian collagen component provides increased resistance to deformation and an increased shear resistance or shear modulus. For example, the collagen component can have a shear modulus in the range of about 10,000 to 200,000 Pascals under the typical conditions of use, and density in the range of about 1.04 to 1.20 g/ml.

In another embodiment, the crosslinked native fibrillar mammalian, avian or reptilian collagen component comprises a resorption rate of about 4 months to about 8 months in situ. In certain implementations, the enhanced carrier material may comprise cross linked native bovine collagen, blended with the microparticles and a gelatinizing agent derived from animal, vegetable, or synthetic sources.

As for composition, the microspheres in accordance with certain implementations of the present invention can comprise a cured polymer, such as a polymethacrylate (PMA), a polymethylmethacrylate (PMMA), a calcium hydroxyapetite (CaHA), Polypropylene (PP), polytetrafluoroethylene (PTFE), hydroxyapetite (HAP), polylactic acid (PLA) beta tricalcium phosphate, calcium phosphate tribasic, hyaluronic acid (HA), polyester, polyvinyl alcohol (PVA), poly lactic co glycolic acid (PLGA), polyetheretherketone (PEEK), polyethylene oxides (PEO), albumin, phopholipids, polyethylene glycols (PEG), calcium alginates, fibrin, polysaccharides, polyoxyesters, polyoxaamides, polyamides, trisacryl gelatin, and copolymers thereof, or any other solid or semisolid biocompatible material. In one implementation, the microparticles can comprise solid microparticles, which may take form in one embodiment of non porous beads. In other implementations, the microparticles may not be altogether solid, such as implementations involving hollow and/or porous microparticles. Said hollow and/or porous microparticles may be used to deliver enhancements to the carrier, including but not limited to, antimicrobial agents, antibiotic agents, anti inflammatory agents, growth factors, or adhesion prevention agents in a time release mechanism. Sacrificial coatings surrounding the hollow and porous microspheres could erode away over time, allowing the release of said agents that were preloaded into the microsphere cores before they were coated.

The microparticles can have a short-term effectiveness of up to about 6 months, a medium term effectiveness of up to about 3 years, or a long term effectiveness of significantly more than 3 years. The microparticles can be made at least in part of biocompatible materials, such as, for example, but not limited to, one or more of any type of collagen, hyaluronic acid (e.g., animal derived, human derived and/or tissue/cell culture derived), genetically altered cells, tissues, organisms, genetically altered or not (e.g., purified cytoskeleton of unicellular and/or multi-cellular algae and/or other organisms), whether cross-linked or not cross-linked, or made of a synthetic and/or polymeric material, such as, for example, polylactic acid, organic compounds, inorganic compounds, ceramic materials, calcium alginates, albumin, beta tricalcium phosphates, phospholipids, polysaccharides, polyoxaesters, polyoxaamide, polyamines, polyethylene glycols (PEG), polyethylene oxides (PEOs), polymethacrylate (PMA), polymethylmethacrylate (PMMA), polypropylene, polytetrafluoroethylene (PTFE), and combinations thereof.

Figure 2:
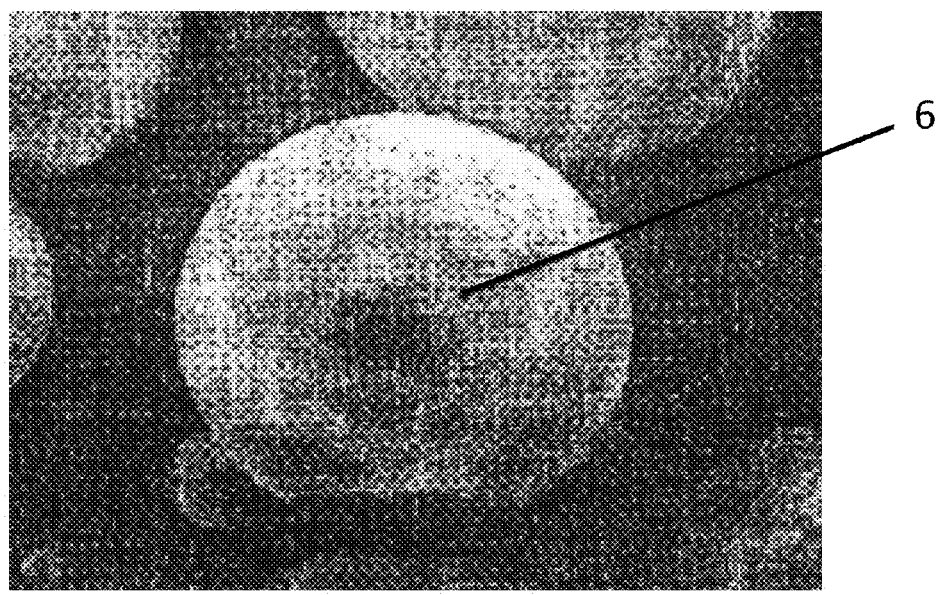
FIG. 2 is an image of a substantially smooth microsphere in accordance with one embodiment of the present invention.
Figure 2:
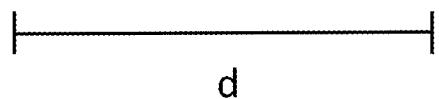

As used herein, the term "microparticles" refers to microparticles (e.g., in a dust or powder form) possessing a mean diameter of at least about 10 microns. Referring to FIG. 2, a microsphere in one embodiment of the present invention can have a smooth surface and a diameter "d". Typically, the average diameter will be greater than about 15 microns rendering the microparticles too large to be consumed by monocytes. The microparticles can have diameters sufficient to keep them from being washed away through lymph tracts or other tissue tracts from the implantation site. If the microparticles do not have a spherical form, then the diameter as used herein may refer to the greatest diameter of the smallest cross sectional area. It is, however, also possible to use different sized (e.g., smaller) microparticles. Typically, the microparticles will have an average diameter less than about 200 microns. In representative embodiments, the microparticles can have an average diameter of about 15 to about 200 microns and in certain implementations from about 15 to about 60 microns. It may be possible in modified embodiments for diameters to range from about 10 microns to about 500 microns. In certain configurations, the microparticles are small enough to be injected from a syringe through a fine gauge cannula or an injection needle to the desired treatment region. Microparticles having the diameters specified herein may have a relatively minimal effect on surrounding tissues.

The microparticles used according to exemplary embodiments of the present invention have smooth or non-turbulent surfaces that are, for example, free from one or more of corners and edges. In similar implementations, the microparticles of these embodiments may be formed at least in part not to have sharp transitions on their surfaces, wherein transitions are for instance found at such corners and edges. In addition, they may be formed not to have peaks of any kind or tapered projections. Consequently, transitions from one outer surface to the other outer surface of one or more of the microparticles as used according to these embodiments of present invention can occur in a continuous manner. If such transitions are present, as is the case for the edges of a cube, such transitions can be smoothed or rounded. Due to the smooth surfaces of the above-described types of microparticles, damage or irritation to cells and other tissue structures can be altered, minimized, or avoided. In addition, according to an aspect of the present invention, the danger of causing reactions of the tissue, such as foreign body reactions or granulous formation in response to sharp edges, which may be followed by infections, can be altered, attenuated, or eliminated.

In addition to spherical forms, the microparticles may comprise, as a few examples, one or more of elliptical (e.g., extruded, molded and/or machined) or cylindrical (e.g., extruded, molded and/or machined) forms, and further may comprise, for example, one or more of smoothed or rounded corners, edges, peaks, and projections. Other implementations may not include smoothed or rounded corners, edges, peaks, and projections.

According to exemplary embodiments of the present invention, microparticles which are crystalline (for instance needle-shaped) or microparticles which have been obtained by mechanically breaking up greater units into smaller pieces, may not be used, in some embodiments, to the extent the microparticles possess the above-mentioned sharp edges and corners. In modified embodiments, these types of microparticles may be used in whole or in part, such as, for example, embodiments comprising microparticles possessing one or more of sizes between about 10 microns and about 500 microns; an absence of smooth surfaces; an absence of corners, edges, peaks, or projections; and an absence of smooth or rounded corners, edges, peaks, and projections.

The microparticles may comprise one or more of a solid body, a porous surface (e.g., a surface impregnated with a material that is subsequently dissolved out), a porous body (e.g., formed by coating an expandable material and then heating, so that the expandable material inside forms a gas and expands forming channels to the surface), a hollow interior (e.g., formed by providing a feed tube into a center of a die for forming a microparticle, whereby as material is passed into the die for molding gas is injected into a central area of the material within the die), a shell-like structure (e.g., formed by coating and/or dissolving-out an interior beneath the coating), a metallic coating, a carbon coating, a carbon nanotube coating, a non-coated surface, components thereof, and combinations thereof in any ratio. According to certain implementations, surfaces of the microparticles of the present invention do not have pores. In other implementations of the present invention, however, parts or all of the surfaces of the microparticles may comprise pores. In certain implementations, dynamically balanced microparticles and in particular instances microparticles having elliptic or spherical forms can be used. In some examples, it is possible to use microparticles of a different geometrical form, and, when in the context of smooth-surfaced implementations, all or a majority of the microparticles may have smooth or smoothed-off surfaces.

When formed with smooth surfaces and the disclosed sizes, the microparticles used may not be detected by the endogenous macrophages as foreign bodies so that no or reduced defensive reactions take place. According to a representative embodiment, the microparticles have spherical forms or sphere-like forms capable of forming closely-packed arrangements at the site where they have been implanted and further capable of being individually encapsulated by scar tissue of the host. For instance, the microparticles, which in a representative embodiment may comprise PMMA spherical beads, after being inserted into the treatment region, may be encapsulated by delicate capsules of connective tissue and/or embedded into connective tissue or fibers where they remain stationary in the tissue.

According to exemplary implementations, regarding maturation of the microparticles, which in a representative embodiment may comprise PMMA spherical beads, as a result of the size and physical stability of the PMMA beads, they cannot be phagocytised or lysed. In order to isolate the foreign body, the animal body can only fibrotically wall off the foreign bodies in the form of scar tissue. Such a process typically takes place with almost any foreign body which cannot be destroyed by the animal body.

To the extent present, the fibrotic growth of connective tissue can be a natural reaction to one or more of the lesion of the tissue caused by the injection cannula (e.g., needle) and the presence of the microparticles. The fibrotic reaction may occur, for example, during 3 to 6 months after injection of the biocompatable augmentation or repair material due, for example, to the smooth and chemically inert surfaces of the microparticles (e.g., PMMA beads). From then on, the beads can remain in the tissue without reaction and provide for the formation and existence of permanent fibrovascular connective tissue.

The microparticles used, according to representative implementations of the present invention, can comprise a polymer, and in particular a completely cured and fully polymerised polymer so that no remaining monomers, which may be toxic or may cause cancer, are incorporated into the body of the treated patient. In principle, it is possible to use any inert histocompatible polymer for producing the microparticles used according to the present invention. Modified embodiments may comprise, in whole or in part, non-polymer microparticles.

Referring to the crosslinking of the native collagen portion of the enhanced carrier, the crosslinking can be accomplished through the addition of energy, or chemical crosslinkers. Crosslinking is the linking of collagen molecules by covalent bonding to polyfunctional polymers. Traditionally, native collagens have been crosslinked using gluteraldehydes in a concentration of roughly 300 ppm. In one preferred embodiment of this invention, it is preferable to utilize glyceraldehydes to achieve the crosslinking, as that crosslinking agent allows the mixture to maintain all of the desirable properties listed above, along with better extrudability than the other crosslinking agents. While glyceraldehyde is one of the preferred chemical crosslinkers, there are many others such as, but not limited to; dialdehyde starch, dimethyl adipimidate, carbodiimide, glucosepane, formaldehyde, gluteraldehyde, pentosidine, polyisocyanates, alginates, sulfhydryls, and genipin. In addition, the crosslinking of the native or fibrillar collagen can be achieved through the addition of energy, in forms such as, but not limited to, convective heat, conductive heat, radiation heat, ultraviolet light, near and far infrared energy, irradiation, sonic and ultrasonic energy.

The control of the ratios of crosslinked and denatured collagen is an important factor in maintaining consistency of the tissue augmenting material. In a preferred embodiment, the biocompatible carrier comprises between about 30% to about 70% crosslinked material. In the preferred embodiment, the crosslinked material will provide a $T_m$ sufficient to maintain a gelatinous state and therefore maintain substantially evenly dispersed microspheres within the biocompatible carrier. As described above, the Tm will be greater than 37.0° C. in the preferred embodiment. The determination of the amount of crosslinking can be achieved through several assays, such as but not limited to the use of differential scanning calorimetry (DSC), or the use of high performance liquid chromatography (HPLC) to determine the crosslinker concentrations and proportional degree of crosslinking that has occurred. It should be noted that the biocompatible carrier comprises a "crosslinked material" being referred to in the past-tense. For simplicity, the "crosslinked material" may be referred to herein as "terminally crosslinked material" since the crosslinking reaction is terminated prior to combining with denatured collagen.

The crosslinked and gelatinous collagens and microspheres and other agents can be blended into a uniform mixture at elevated temperatures, and then cooled to a semisolid or gelatinous state. The mixture can be stored at room temperatures and beyond if necessary for subsequent introduction (e.g. injection) into a patient. Generally, various types of processing may be implemented on the enhanced carrier and/or otherwise, at various points in time and/or various locations. For example, the injection apparatus may be operated in conjunction with a micronizing function, which, for example, may be implemented with one or more of structure configured to perform physical micronization (e.g., by way of a rotating cutter disposed in the usable volume of the syringe or delivery system barrel, or forcing the material through meshes or small orifices) and structure configured to perform ultrasonic micronization (e.g., by way of application of ultrasonic energy from an external source to the usable volume of the system barrel), a component of either, and combinations thereof. Additionally, or alternatively, any implementation of the syringe or delivery system described herein may be operated in conjunction with a filtering function, such as, for example, an implementation wherein the enhanced carrier (or, in modified embodiments, tissue, cells and/or fluid) is passed through a sterile filter (e.g., a 0.2 micron filter to remove microorganisms) formed within or in conjunction with a syringe or other delivery system, for example, before mixing with microparticles.

Some components of the enhanced carrier solution, herein referred to as carrier components, may include agents such as but not limited to, a crosslinking agent, an agent to assist in homogeneity, a coagulant agent, a growth factor, a hemostatic agent, a radiopaque indicator agent, a photosensitive dye agent, a contrasting agent, stem cells, an agent to facilitate bonding, an adhesion prevention agent, an antibiotic agent, an anesthetic agent, an anti-inflammatory agent, a gelatin (harvested, added in the form of a powder, or in the form of a gelatinous media, any of which can be from the host, synthetic, or from another organism or animal source or vegetable source), or a combination including one or more of the preceding components, or other materials which are capable of for example being introduced into a second sterile injection syringe and injected through a mixer in parallel with the other components before being injected into the body to achieve a suitable or optimal correction of an issue or problem.

The mixing ratio of the components of the enhanced carrier (e.g., crosslinked collagen material and gelatinous carrier material and microspheres) can be controlled and dictated according to the physiological and delivery needs, and in particular according to the density of the tissue and the size of the microspheres used for the injection. For the application or injection of the microparticles used according to an embodiment of the present invention, the microparticles can be 5% to 80% of the mixture by weight. The crosslinked collagen component can be 5% to 90% of the mixture by weight. The gelatinous component of the mixture can be 5% to 90% of the mixture by weight.

The administering of the tissue treatment implant can be performed on, for example, humans and animals (e.g., horses, dogs, and cats) and can comprise, for example, treating or augmenting tissue, such as, for example, one or more of augmenting a skin defect and/or cosmetically enhancing a facial feature; enhancing penile, breasts, or clitoral; bulking one or more of a vocal cord, a lower esophageal sphincter to control gastroesaphageal reflux disease (GERD), a pyloric sphincter, a bladder sphincter and an anal sphincter to relieve urinary or fecal incontinence; occluding the fallopian tubes, vas deferens, or reproductive organs or passageways to achieve an infertile condition; repair of vasculature; repair of the aortic valve, mitral valve, tricuspid valve, pulmonary valve, or other coronary valves; repair of the heart or other organs; repair of ulcerous organs or passageways; occluding a vascular supply to a tumor; tumor metastasis or tumor embolization by way of, for example, blocking a vascular flow exiting a tumor; tumor embolization by intratumor application, blocking a vascular supply to a tumor, blocking a vascular flow exiting the tumor, and/or combinations thereof, a repair or augmentation of a vertebral disk; bulking or repair of muscles, bulking or repair of tendons, bulking or repair of the gums, bulking of the cornea or repair of the optic nerve or other optic anatomy, repair of plantar facia loss in the base of the foot, cartilage augmentation, cartilage repair, synovial fluid replenishment and/or combinations thereof, and administration of the tissue implant to one or more of nasal cartilage, for minimally invasive rhinoplasty or for the treatment of sleep apnea, ear cartilage, elbow, hip, or knee joint cartilage, spinal cord cartilage, and combinations thereof.

Following insertion (e.g., injection) of the biocompatible augmentation or repair material into a region or regions of interest, the biocompatible augmentation or repair material in accordance with one aspect of the present invention may in certain implementations begin to undergo a complete or at least partial biodegradation of, for example, the biocompatible medium (e.g., the enhanced carrier material). In accordance with a typical implementation, following insertion of the biocompatible augmentation or repair material, the enhanced carrier material is at least partially and, preferably substantially, resorbed into or via tissues of the host mammalian body and/or replaced or supplemented with host tissue (e.g., host collagen). In a representative embodiment, the biocompatible carrier medium is both resorbed and replaced with host tissues.

In one aspect of the present invention, a system for delivery of a tissue augmenting material comprises a syringe delivery system and a material for injection. Referring to FIG. 1, in one embodiment of the present inventions, the material for injection 4 can be stored in and delivered by a syringe delivery system. The syringe delivery system can comprise a syringe barrel 2 with attached finger flanges 3, a plunger and a plunger rod 5, and a needle 1. The material for injection 1 can comprise a biocompatible carrier, and an amount of evenly-distributed suspended microparticles. The biocompatible carrier can comprise at least one crosslinked material and a partially-denatured gelatinous collagen and/or other biocompatible gelatinous material. The crosslinked material can be selected or manufactured to provide the material for injection with a $T_m$ in the range of about 37° C. to about 65° C. A $T_m$ in this range will allow the material for injection to maintain a gelatinous state in situ as well as during storage of the product, and therefore sufficiently maintain a substantially even distribution of the suspended microparticles without the cost detriment due to a need for refrigeration. Additionally, this system will provide a product capable of shipping without the need for refrigeration and time-sensitive delivery.

In one aspect of the present invention, a method for manufacturing a material for tissue augmentation comprises, providing a crosslinked material and a gelatinous collagen in an aseptic environment, combining an amount of the crosslinked collagen with an amount of gelatinous collagen or other biocompatible gelatin to form a biocompatible carrier, heating the biocompatible carrier to form a liquid mixture, introducing an amount of microparticles, suspending said particles by rotation or other mixing technique, and cooling the composition below 37° C.

While this invention has been described with respect to various specific examples and embodiments, it is to be understood that the invention is not limited thereto and that it can be variously practiced. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. For example, alternate means of manufacturing the enhanced carriers, microspheres, cells, or fluids may be employed, and they are not limited to those described above. In addition, the methods of processing (e.g., micronizing) the enhanced carrier, cells, or fluids, and the means of mixing the components of the tissue augmentation and/or repair materials can be varied, or the assisting materials that are preloaded into the delivery system can be reduced or expanded to exclude or include any number of additives or chemical or biological agents. Accordingly, the present invention should not be limited by the disclosed embodiments, but is to be defined by reference to the appended claims.

What is claimed is:

1. A composition for tissue augmentation, comprising: a biocompatible carrier and an amount of microparticles suspended within said biocompatible carrier; said biocompatible carrier comprising a controlled ratio mixture of: terminally crosslinked material and biocompatible gelatin material wherein said crosslinked material comprise from about 5% to about 90% of the composition by weight, adapted to provide a composition melting temperature between 37° C. and 65° C.; wherein said biocompatible carrier is adapted to maintain said microparticles in suspension therein at temperatures between 37° C. and said melting temperature.

2. The composition of claim 1, wherein said microparticles are substantially uniformly suspended within said biocompatible carrier at ambient temperature.

3. The composition of claim 1, wherein said microparticles have a substantially smooth surface.

4. The composition of claim 1, said microparticles comprising at least one of a biocompatible polymer, elastomer, gelatin, or ceramic.

5. The composition of claim 4, wherein said biocompatible polymer is selected from the group consisting of; albumin, polymethacrylate (PMA), polymethylmethacrylate (PMMA), beta tricalcium phosphate, calcium alginates, calcium hydroxylapetite (CaHA), calcium phosphate tribasic, fibrin, phospholipids, polyethylene oxides (PEOs), polysaccharides, polyamines, polyoxaamides, polyoxaesters, polyethylene glycol (PEG), polypropylene (PP), polytetrafluoroethylene (PTFE), hydroxyapetite (HAP), hyaluronic acid (HA), polylactic acid (PLA), polyester, polyvinyl alcohol (PVA), poly lactic co glycolic acid (PLGA), polyetheretherketone (PEEK), trisacryl gelatin, and copolymers thereof.

6. The composition of claim 1, wherein said microparticles are at least partially biodegradable.

7. The composition of claim 1, wherein said biocompatible polymer contains an imaging enhancement material, such as radiopaque indicators, dye markers, or other contrasting agent(s).

8. The composition of claim 1, wherein said biocompatible carrier comprises one or more of: mammalian, reptilian, or avian collagen, a Polysaccharide gel, and hyaluronic acid gel.

9. The composition of claim 1, wherein said crosslinked material comprises one or more of: a crosslinked Polysaccharide gel, crosslinked carboxymethyl cellulose, and crosslinked hyaluronic acid.

10. The composition of claim 1, wherein said biocompatible carrier further comprises at least one carrier component, and wherein said carrier component is at least one of; a crosslinking agent, an agent to assist in homogeneity, a coagulant agent, a growth factor, a hemostatic agent, an agent to facilitate bonding, an adhesion prevention agent, an antibiotic agent, an anesthetic agent, an anti-inflammatory agent, a radiopaque indicator agent, a dye agent, a contrasting agent, animal derived gelatin, vegetable derived gelatin, or a chemically synthesized gelatin.

11. The composition of claim 1, wherein said microparticles individually comprise a diameter between about 15 microns and about 200 microns.

12. A method for manufacturing a composition for tissue augmentation, said method comprising; combining a controlled ratio mixture of terminally crosslinked collagen and an amount of denatured collagen wherein said crosslinked material comprises from about 5% to about 90% of the composition by weight, wherein said mixture forms a biocompatible collagen carrier and said composition having has a composition melting temperature between 37° C. and 65° C.; heating the compatible collagen carrier above the composition melting temperature to form a liquid mixture; introducing an amount of microparticle into said liquid mixture; stirring the liquid mixture to uniformly suspend the microparticles therein, and cooling the liquid mixture below 37° C. to form a semisolid gel having said microparticles uniformly suspended therein.

13. The method of claim 12, comprising: crosslinking collagen with glyceraldehyde to form the terminally crosslinked collagen.

14. A composition for tissue augmentation, comprising: a plurality of microparticles suspended within a biocompatible carrier; characterized in that: said biocompatible carrier of denatured collagen wherein said crosslinked material comprises from about 5% to about 90% of the composition by weight, and is adapted to yield a composition melting temperature between 37° C. and 65° C.; said terminally crosslinked collagen comprises an amount of collagen crosslinked with glyceraldehyde to provide a shear modulus between 10.0 and 200.0 kilopascals; and said biocompatible carrier being a semisolid gel at elevated temperatures between room temperatures and said melting temperature such that said biocompatible carrier is adapted to maintain the plurality of microparticles in suspension at said elevated temperatures.

15. The composition of claim 14, wherein the composition for tissue augmentation is adapted for extrusion through a syringe needle.

* * * * *